United States Patent [19]

Duc et al.

[11] Patent Number: 4,788,294

[45] Date of Patent: Nov. 29, 1988

[54] PROCESS FOR THE PRODUCTION OF 4-ALKOXY-3-PYRROLIN-2-ONES

[75] Inventors: Laurent Duc, Sion; John McGarrity; Thomas Meul, both of Visp, all of Switzerland

[73] Assignee: Lonza Ltd., Gampel/Valais, Switzerland

[21] Appl. No.: 170,702

[22] Filed: Mar. 14, 1988

Related U.S. Application Data

[63] Continuation of Ser. No. 907,011, Sep. 15, 1986, abandoned.

[30] Foreign Application Priority Data

Jun. 19, 1986 [CH] Switzerland ................. 2486/86

[51] Int. Cl.$^4$ ............................................ C07D 207/38
[52] U.S. Cl. ........................................................ 548/544
[58] Field of Search ......................................... 548/544

[56] References Cited

U.S. PATENT DOCUMENTS

| | | | |
|---|---|---|---|
| 2,535,010 | 12/1950 | Croxall et al. | 560/183 |
| 2,784,191 | 3/1957 | Fischer et al. | 548/554 |
| 4,118,396 | 10/1978 | Pifferi et al. | 260/326.43 |
| 4,124,594 | 11/1978 | Monguzzi et al. | 260/326.43 |
| 4,173,569 | 11/1979 | Banfi et al. | 260/326.43 |

FOREIGN PATENT DOCUMENTS

| | | | |
|---|---|---|---|
| 192255 | 1/1986 | European Pat. Off. | |
| 850007 | 5/1952 | Fed. Rep. of Germany | |
| 0183756 | 11/1982 | Japan | 548/544 |

OTHER PUBLICATIONS

C. A. MacKenzie et al., J.O.C.S., 20, No. 12 (1955), p. 1695.
Koehler, "Synthesis of Dysidin", Dissertation, Univ. of Bayreuth, Germany (1985).
Pifferi et al., Il Farmaco, Ed. Soc., (1977), 32, pp. 602 to 613.
Cram et al., J. Am. Chem. Soc., 1963, 85, pp. 1430–1437.
Ho et al., "Cleavage of Esters and Ethers with Iodotrimethylsilane", Angewandte Chemie, vol. 15, No. 12, (Dec. 1976), pp. 774 and 775.
Chemical Abstracts CA:105:226341.
Lowe, J. Chem. Soc., Perkin Trans. I, 1973, 2907–2910.
Sidgwick, "The Organic Chemistry of Nitrogen", 3rd Ed., Oxford (1966), p. 637.

*Primary Examiner*—Glennon H. Hollrah
*Assistant Examiner*—D. B. Springer
*Attorney, Agent, or Firm*—Fisher, Christen & Sabol

[57] ABSTRACT

Process for the production of 4-alkoxy-3-pyrrolin-2-ones, which are preferred intermediate products for the production of cerebrally-active pharmaceutical products.

1 Claim, No Drawings

PROCESS FOR THE PRODUCTION OF 4-ALKOXY-3-PYRROLIN-2-ONES

This application is a continuation of application Ser. No. 907,011, filed Sept. 15, 1986, now abandoned.

The subject application is related to the commonly-owned application Ser. No. 907,012 entitled, "4-alkoxy-3-pyrrolin-2-on-1-yl acetic acid alkyl esters and their production", which was filed on Sept. 15, 1986 on the same date. The commonly-owned application Ser. No. 907,012 are incorporated herein by reference.

BACKGROUND OF THE INVENTION

1. Field of the Invention

The invention relates to a new process for the production of 4-alkoxy-3-pyrrolin-2-ones.

2. Prior Art 4-alkoxy-3-pyrrolin-2-ones are valuable, stable intermediate products for the synthesis of cerebrally-active 4-hydroxy-2-oxo-pyrrolidin-1-yl acetamide. It is known to produce the intermediate product by starting from 4-chloro aceto acetic acid methyl ester according to Koehler, Dissertation Bayreuth, (1985), in a yield of 15 percent. The poor yield, which does not allow any reasonable hope for an economically profitable process, is particularly disadvantageous.

BROAD DESCRIPTION OF THE INVENTION

The main object of the invention is to provide a more advantageous method of producing 4-alkoxy-3-pyrrolin-2-ones than the above-described prior art method. Other objects and advantages of the method of the invention are set out herein or are obvious herefrom to one skilled in the art.

The objects and advantages of the invention are achieved by the method of the invention.

The invention involves a process for the production of a 4-alkoxy-3-pyrrolin-2-one having the formula:

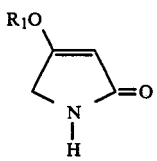

wherein $R_1$ is a $C_1$ or $C_2$ alkyl group. The process includes reacting a 4-halo aceto acetic acid-($C_1$-$C_4$)-alkyl ester with an orthoformic acid-($C_1$-$C_2$)-trialkylester in an acid medium. The resultant 4-halo-3,3-di-[($C_1$-$C_2$)alkoxy]-butyric acid-($C_1$-$C_4$)-alkyl ester is converted by heating in a vacuum to a 4-halo-3-($C_1$-$C_2$)-alkoxy-2-E-butenoic acid-($C_1$-$C_4$)-alkyl ester. The latter ester can optionally be isolated. Then, the latter ester is reacted with aqueous ammonia to produce the end product.

For production of the acid medium, inorganic acids, such as sulfuric acid or sulfonic acids, for example, methanesulfonic acid, are advantageously used. Sulfuric acid is preferably used. In relation to 1 mol of the 4-halo aceto acetic acid-($C_1$-$C_4$)-alkyl ester used, 0.01 to 0.1 mol of the corresponding acid is advantageously used.

The reaction temperature in the first stage of the production of the 4-halo-3,3-di-[($C_1$-$C_2$)-alkoxy]butyric acid-($C_1$-$C_4$)-alkyl ester is preferably between 0° and 30° C. The reaction temperature in the second stage of the production of 3-($C_1$-$C_2$)-alkoxy-2-E-butenoic acid-($C_1$-$C_4$)-alkyl ester is advantageously between 100° and 160° C. (at a pressure of 50 to 200 mbar).

The resultant 3-($C_1$-$C_2$)-alkoxy-2-E-butenoic acid-($C_1$-$C_4$)-alkyl ester can be isolated, but preferably it is further reacted directly with aqueous ammonia solution to produce the end product. For this purpose, the procedure is generally such that the volatile reaction products are removed from the reaction mixture of the first stage by vacuum distillation. By heating in a vacuum, the cleavage of the methanol from the intermediately produced ketal is achieved in the second stage. The residue then is mixed with aqueous ammonia solution having an $NH_3$ content of advantageously 10 to 25 percent, preferably 15 to 25 percent. The reaction temperature is advantageously between 20° and 100° C., preferably between 60° and 80° C. The molar ratio of 4-halo-3-($C_1$-$C_2$)-alkoxy-2-E-butenoic acid-($C_1$-$C_4$)-alkyl ester to $NH_3$ is advantageously between 1 to 2 and 1 to 5, preferably between 1 to 2.5 and 1 to 3.5.

After the usual working up, e.g., by extraction with a suitable solvent from the group of halogenated hydrocarbons, such as, methylene chloride and chloroform, the corresponding 4-($C_1$-$C_2$)-alkoxy-3-pyrrolin-2-one can be obtained in good yield. Optionally, it can be additionally purified by, for example, recrystallization in an aromatic hydrocarbon, preferably toluene.

Preferably, 4-methoxy-3-pyrrolin-2-one is produced according to the invention process, starting from 4-chloro aceto acetic acid methyl ester.

DETAILED DESCRIPTION OF THE INVENTION

As used herein, all parts, percentages, ratios and proportions are on a weight basis unless otherwise stated herein or obvious herefrom to one ordinarily skilled in the art.

THE EXAMPLE

Production of 4-methoxy-3-pyrrolin-2-one

A solution of 63.3 g (0.409 mol) of 4-chloro aceto acetic methyl ester and 54.0 g (0.508 mol) of orthoformic acid methyl ester were cooled to 10° C. and, within 10 minutes, mixed, with stirring, with 2.0 g (0.02 mol) of concentrated $H_2SO_4$. Stirring was again performed for 5 hours at room temperature. Then the volatile products were distilled off from the intermediately resultant 4-chloro-3,3-di-methoxy-butyric acid methyl ester in a vacuum of 25 mbar. Then the residue was heated at 125° C. and at 100 mbar for 2.5 hours. During this period, 10.5 g of methanol distilled off. The residue, consisting of 4-chloro-3-methoxy-2-E-butenoic acid methyl ester, was added drop by drop within 1.75 hours at 64° to 68° C. to a solution of 121.3 g of (17 percent) concentrated $NH_3$ solution in 83.7 g of water. After half of the addition, 24.3 g of (17 percent) concentrated $NH_3$ solution was added. After the addition was completed, the reaction solution was stirred again for 45 minutes at 65° C. Then the reaction solution was cooled to room temperature and continuously (for 12 hours) extracted with 300 ml of methylene chloride. The methylene chloride solution was dried over $Na_2SO_4$ and filtered off. After evaporation of the solution under vacuum, the crystalline residue was recrystallized, while hot, from 150 ml of toluene. 40.8 g of white, crystalline product having a melting point of 130° to 132° C. [content (GC): 99.0 percent] was obtained. This corresponded to a yield of 87.4 percent.

What is claimed is:
1. In the process for the production of a 4-alkoxy-3-pyrrolin-2-one having the formula:

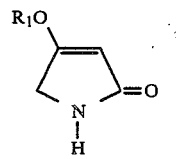

wherein $R_1$ is a $C_1$ or $C_2$ alkyl, consisting of the ammonolysis of 4-halo-3,3-di-[($C_1$–$C_2$)-alkoxy]-butyric acid-($C_1$–$C_4$)-alkyl ester, the improvement of effecting said ammonolysis by contacting said 4-alkoxy-3-pyrrolin-2-one and an aqueous ammonia solution having an $NH_3$ content of 10 to 25 percent at a temperature of 20° to 100° C.

* * * * *